United States Patent
Minai et al.

(10) Patent No.: US 7,398,117 B2
(45) Date of Patent: Jul. 8, 2008

(54) SYSTEM FOR DETECTING POSITION OF CAPSULE ENDOSCOPE IN SUBJECT

(75) Inventors: Tetsuo Minai, Tokyo (JP); Hatsuo Shimizu, Tokyo (JP)

(73) Assignee: Olympus Corporation, Tokyo (JP)

( * ) Notice: Subject to any disclaimer, the term of this patent is extended or adjusted under 35 U.S.C. 154(b) by 343 days.

(21) Appl. No.: 11/019,029

(22) Filed: Dec. 21, 2004

(65) Prior Publication Data
US 2005/0143642 A1 Jun. 30, 2005

(30) Foreign Application Priority Data
Dec. 26, 2003 (JP) ............................. 2003-435556

(51) Int. Cl.
*A61B 5/05* (2006.01)
(52) U.S. Cl. .................... 600/424; 600/101; 600/117
(58) Field of Classification Search ................. 600/424, 600/101, 103, 117, 160
See application file for complete search history.

(56) References Cited

U.S. PATENT DOCUMENTS

| | | | |
|---|---|---|---|
| 5,681,260 A | | 10/1997 | Ueda et al. |
| 6,427,314 B1 * | | 8/2002 | Acker .......................... 29/593 |
| 7,039,453 B2 * | | 5/2006 | Mullick et al. .............. 600/476 |
| 2002/0173718 A1 | | 11/2002 | Frisch et al. |
| 2004/0143182 A1 * | | 7/2004 | Kucera et al. ............... 600/424 |
| 2005/0139222 A1 * | | 6/2005 | Minai et al. ................. 128/899 |

FOREIGN PATENT DOCUMENTS

| | | |
|---|---|---|
| JP | 4-8341 | 1/1992 |
| JP | HEI-9-28662 A | 2/1997 |
| JP | 9-94257 | 4/1997 |
| JP | HEI-10-230016 A | 9/1998 |
| JP | 2001-46357 A | 2/2001 |
| JP | 2001-179700 A | 7/2001 |
| JP | 2003-019111 | 1/2003 |
| JP | 2003-117004 A | 4/2003 |

* cited by examiner

*Primary Examiner*—Jacqueline Cheng
(74) *Attorney, Agent, or Firm*—Scully, Scott, Murphy & Presser, P.C.

(57) ABSTRACT

A system includes a device that is swallowed, passes through a subject, and includes a magnetic field generator generating a constant magnetic field; and a position transducer. The position transducer includes a magnetic detector detecting a magnetic filed, a magnetic field extractor extracting the constant magnetic field output from the magnetic field generator by removing a noise magnetic field component from the magnetic field detected by the magnetic detector, and a position processor calculating a position of the device in the subject based on an intensity of the constant magnetic field extracted by the magnetic field extractor.

15 Claims, 11 Drawing Sheets

US 7,398,117 B2

SYSTEM FOR DETECTING POSITION OF CAPSULE ENDOSCOPE IN SUBJECT

CROSS-REFERENCE TO RELATED APPLICATIONS

This application claims the benefit of priority of Japanese Patent Application No. 2003-435556 filed in Japan on Dec. 26, 2003, and the disclosure of which is incorporated herein by its entirety.

BACKGROUND OF THE INVENTION

1) Field of the Invention

The present invention relates to a system for detecting a position of a device such as a capsule endoscope, which is swallowed and passes naturally through the digestive tract of the subject, by a position transducer that is disposed on the outside of the subject and obtains information of the position of the device in the subject.

2) Description of the Related Art

In recent years, in the field of endoscopes, a swallowable capsule endoscope has been proposed. The capsule endoscope has an image capturing function and a radio communication function. The capsule endoscope has the function of traveling in the body cavity, for example, in the organs such as the stomach and the small intestine with peristalsis of the organs and sequentially capturing images for a period of time since the capsule endoscope is swallowed from the mouth of a subject for inspection (examination) until it is naturally excreted.

Image data captured in the body by the capsule endoscope as the capsule endoscope travels in the body cavity is sequentially transmitted by radio communication to the outside and stored into a memory provided on the outside. The subject can freely move throughout the period after he/she swallows the capsule endoscope until it is excreted by carrying a receiver having a radio communication function and a storing function. After the capsule endoscope is excreted, a doctor or nurse can display the images of the organs on a display based on the image data stored in the memory and make a check.

A capsule endoscope has been proposed in which the receiver has the function of detecting the position of the capsule endoscope in the subject to capture, for example, an endoscope image of a specific organ in the subject. As an example of a capsule endoscope system having the position detecting function, a capsule endoscope system using the radio communication function provided in the capsule endoscope is known. Specifically, the system has a configuration that a receiver provided on the outside of a subject has a plurality of antenna elements, and has the function of receiving a radio signal transmitted from the capsule endoscope by the plurality of antenna elements and, based on intensities received by the antenna elements, detecting the position of the capsule endoscope in the subject (see Japanese Patent Application Laid-open No. 2003-19111, for example).

SUMMARY OF THE INVENTION

It is an object of the present invention to at least solve the problems in the conventional technology.

According to an aspect of the invention, provided is a system comprising a device that is swallowed, passes through a subject to collect information on the subject, and includes a magnetic field generator generating a magnetic field of a predetermined intensity and a position transducer which provides the position of the device based on the magnetic field. The position transducer includes a plurality of magnetic detectors, disposed substantially at vertexes of a hypothetical cube circumscribing a part of the subject, for each detecting a magnetic field caused by the magnetic field generator; a storage unit that stores at least an intensity of a noise magnetic field component detected by each of the magnetic detectors with the magnetic detectors so oriented as to enable a parallel displacement thereof onto a predetermined coordinate system; a magnetic field extractor for coordinate-transforming the noise magnetic field components on the basis of a relationship between the predetermined coordinate system and a current coordinate system expended by selected ones of the magnetic detectors, and for extracting a magnetic field at each magnetic detector which magnetic field is caused by the magnetic field generator by removing a coordinate-transformed noise magnetic field component associated with detected magnetic fields detected by the selected magnetic detectors from the detected magnetic field detected by the magnetic detector; and a position processor for calculating a position of the device in the subject based on intensities of extracted magnetic fields extracted by the magnetic field extractor. The system utilizes collected information obtained from the device by associating the collected information with the calculated position of the device.

The other objects, features, and advantages of the present invention are specifically set forth in or will become apparent from the following detailed description of the invention when read in conjunction with the accompanying drawings.

DETAILED DESCRIPTION

Figure 1:
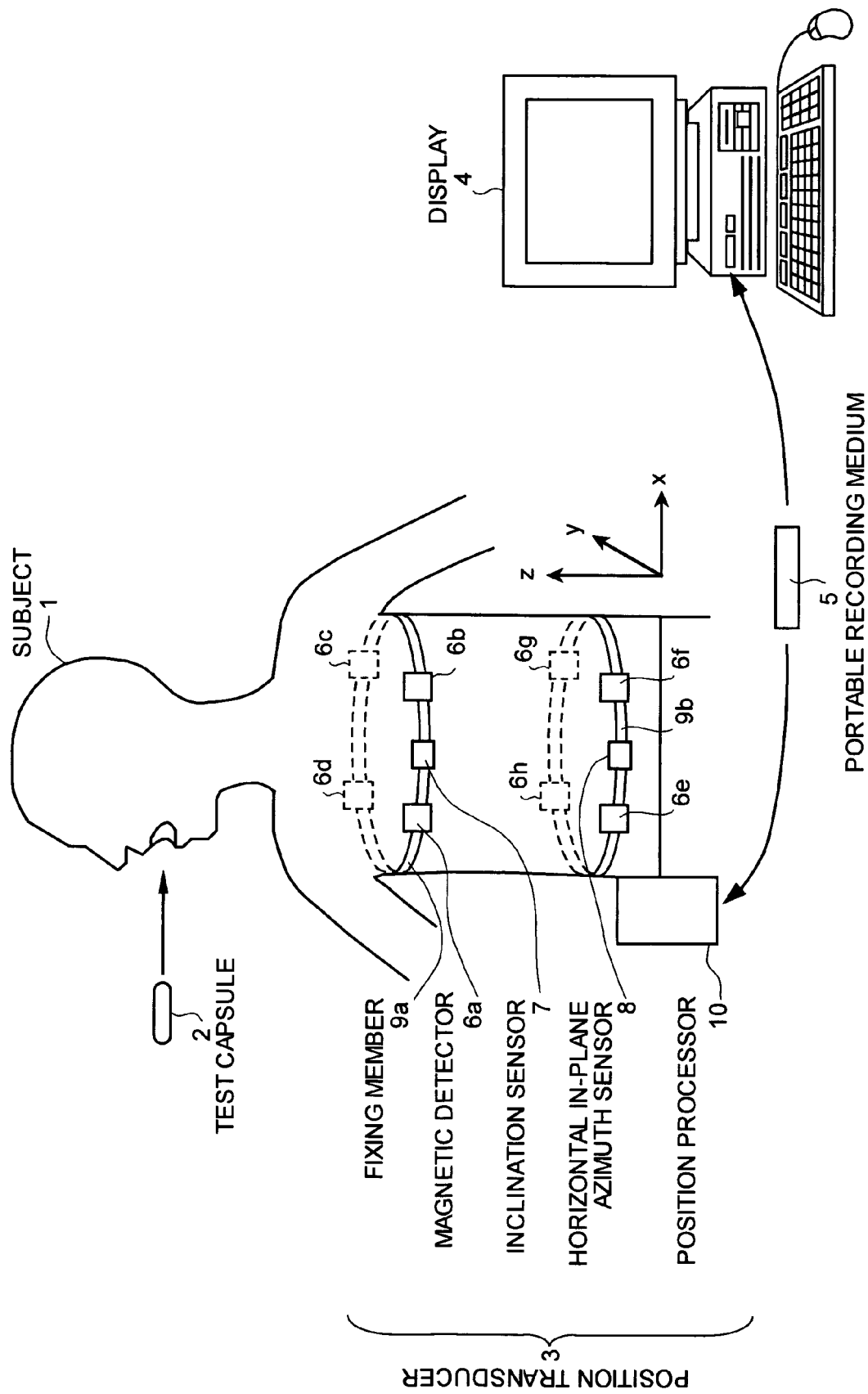
FIG. 1 is a schematic view of a system for detecting a position of a capsule endoscope in a subject according to a first embodiment.

Exemplary embodiments of a system for detecting a position of a capsule endoscope in a subject relating to the present invention will be explained in detail below with reference to the accompanying drawings. It should be noted that the drawings are schematic ones and the relation between thickness and width of each part, the thickness ratio of the parts, and the like are different from real ones. Obviously, the drawings include parts having different relations of dimensions and ratios.

A system for detecting a position of a capsule endoscope in a subject according to a first embodiment will now be explained. The system for detecting a position of a capsule endoscope according to the first embodiment of the present invention includes a test capsule 2 that is swallowed and passes though a subject 1 and functions as an example of a device to be traveled in a subject; a position transducer 3 that detects the position in the subject 1 of the test capsule 2; a display 4 displaying position information of the test capsule 2 detected by the position transducer 3; and a portable recording medium 5 for transmitting/receiving information between the position transducer 3 and the display 4.

The display 4 is used for displaying position information of the test capsule 2 obtained by the position transducer 3 and has a configuration like a workstation or the like that displays an image based on data obtained from the portable recording medium 5. Concretely, the display 4 may be constructed to directly display an image by a cathode-ray tube (CRT) display, a liquid crystal display, or the like or to output an image to another medium like a printer or the like.

The portable recording medium 5 can be inserted/removed to/from a position processor 10 that is explained later and the display 4, and has a structure capable of outputting and recording information when inserted to the position processor 10 and the display 4. Concretely, the portable recording medium 5 is inserted in the position processor 10 to record information on the position of the test capsule 2 while the test capsule 2 travels in the body cavity of the subject 1. After the test capsule 2 is excreted from the subject 1, the portable recording medium 5 is removed from the position processor 10 and inserted into the display 4, and the recorded data is read by the display 4. By transmitting data between the position processor 10 and the display 4 by the portable recording medium 5 such as a compact flash (trademark) memory, different from the case where the position processor 10 and the display 4 are connected to each other by wire, even when the test capsule 2 is traveling in the subject 1, the subject 1 can move freely.

The test capsule 2 is used at the time of conducting a preliminary inspection to check whether or not a narrow part in which passage of a capsule endoscope is difficult exists in the subject 1 before introduction of the capsule endoscope or the like into the subject 1. The system according to the first embodiment is used to check how the test capsule 2 travels in the subject 1. To achieve the purpose, a high-precision position detecting mechanism is provided.

Figure 2:
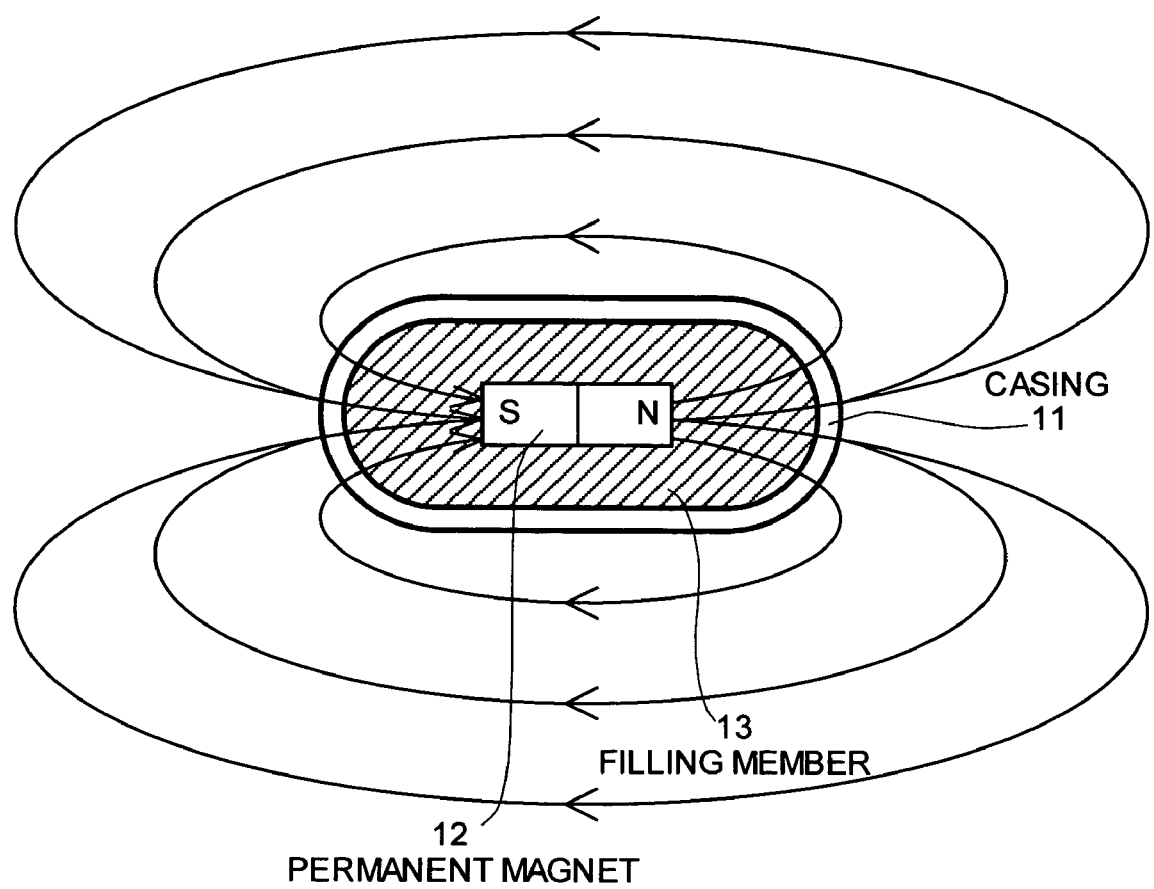
FIG. 2 is a schematic view of a test capsule as a component of the system according to the first embodiment.

FIG. 2 is a schematic diagram of the test capsule 2. As shown in FIG. 2, the test capsule 2 includes a casing 11 having a capsule shape that is similar to that of a casing of a capsule endoscope; a permanent magnet 12 disposed in the casing 11; and a filling member 13 serving to fill the clearance between the inner surface of the casing 11 and the permanent magnet 12.

The casing 11 is made of, for example, a bio-compatible material and has a characteristic such that when the casing 11 remains in the subject 1 for a few days, the material dissolves. By forming the casing 11 of a bio-compatible material, there is an advantage such that even if the test capsule 2 introduced in the subject 1 is not excreted to the outside of the subject 1, it is unnecessary to perform an abdominal operation or the like on the subject 1.

The permanent magnet 12 functions as a magnetic field generator in the claims, has a size that can be housed in the casing 11, and is to output a constant magnetic field whose intensity fluctuation with time is ignorable. In place of the permanent magnet 12, for example, a coil that receives constant current and generates a constant magnetic field may be used as the magnetic field generator. In the case of using the permanent magnet 12, there is an advantage such that drive power is unnecessary. Thus, it is preferable to construct the magnetic field generator by using the permanent magnet 12.

As shown in FIG. 2, the constant magnetic field generated from the permanent magnet 12 is expressed by a line of magnetic force of a closed curve that is output from the N pole side, travels on the outside of the permanent magnet 12, and enters again on the S pole side. As shown in FIG. 2, the travel direction of the line of magnetic force has location dependency but it can be regarded that the intensity of the constant magnetic field expressed by the line of magnetic force is determined only in accordance with the distance from the test capsule 2. Specifically, the size of the permanent magnet 12 provided in the test capsule 2 is small enough to be ignored as compared with the distance between the test capsule 2 and magnetic detectors 6a to 6h. Consequently, magnetic field intensity P at a point apart from the test capsule 2 only by distance "r" is expressed as follows by using a proportional factor α.

$$P = \alpha/r^3 \quad (1)$$

The system according to the first embodiment detects the position of the test capsule 2 based on the relation shown in Equation (1) as is explained later.

The filling member 13 is provided to fill the clearance between the inner face of the casing 11 and a permanent magnet 12 to fix the position of the permanent magnet 12. The material of the filling member 13 does not exert an adverse influence on the subject 1. For example, the filling member 13 is made of barium sulfate. Since barium sulfate can be used as a contrast medium in an X-ray inspection, position detection by an X-ray inspection can be performed in addition to the position detection of the first embodiment. By comparing the results of both of the inspections, more accurate position detection can be performed. Obviously, it is not essential to use barium sulfate as the filling member 13 in the first embodiment and an arbitrary material can be used as long as the material functions as the filling member.

The position transducer 3 is explained. The position transducer 3 detects the position of the test capsule 2 in the subject 1 based on the constant magnetic field output from the test capsule 2. Concretely, the position transducer 3 has, as shown in FIG. 1, the magnetic detectors 6a to 6h for detecting the intensity of the constant magnetic field output from the test capsule 2, an inclination sensor 7 for detecting the degree of inclination of the subject 1, a horizontal in-plane azimuth sensor 8 for detecting the orientation direction of the subject 1 in a horizontal plane, a fixing member 9a for fixing the magnetic detectors 6a to 6d and the inclination sensor 7 to the subject 1, a fixing member 9b for fixing the magnetic detectors 6e to 6h and the horizontal in-plane azimuth sensor 8 to the subject 1, and the position processor 10 for calculating the position of the test capsule 2 based on the magnetic field intensities detected by the magnetic detectors 6a to 6h.

Each of the magnetic detectors 6a to 6h is to detect the magnetic field direction and intensity in the position where it is disposed, for example. More specifically, each of the magnetic detectors 6a to 6h is constructed by a Magneto Impedance (MI) sensor, for example. The MI sensor has a configuration using, for example, an FeCoSiB amorphous wire as a magneto-sensitive medium and senses the magnetic field intensity by using an MI effect that the magnetic impedance of the magneto-sensitive medium largely changes according to an external magnetic field when high-frequency current is passed to the magneto-sensitive medium. The magnetic detectors 6a to 6h may be constructed by other magnetic sensors, though the MI sensor provides particularly highly sensitive magnetic intensity detection.

The magnetic detectors 6a to 6h are disposed in positions at vertexes of a cube in the first embodiment, respectively, and an xyz coordinate system is determined as shown in FIG. 1 in correspondence with the sides of the cube. That is, when the magnetic detector 6e is set as the origin, the direction from the magnetic detector 6e toward the magnetic detector 6f is set as the x axis, the direction from the magnetic detector 6e toward the magnetic detector 6h is set as the y axis, and the direction from the magnetic detector 6e toward the magnetic detector 6a is set as the z axis. It is assumed that the magnetic detectors 6a to 6h output magnetic field components parallel to the x axis, y axis, and z axis to a magnetic field extractor 15. As described later, the absolute directions of the xyz coordinate system change according to a change in the posture of the subject 1 or the like. Consequently, a fixed absolute coordinate system is defined as an x'y'z' coordinate system and description will be given so as to distinguish the xyz coordinate system and the x'y'z' coordinate system from each other as necessary. In the x'y'z' coordinate system, the direction of the z' axis is set to the vertical direction.

The inclination sensor 7 is used to sense the inclination degree of the subject 1 and functions as a mode of a vertical direction sensor in the claims. Specifically, the inclination sensor 7 has the function of detecting the angle formed between a predetermined reference direction and the vertical direction. The inclination sensor 7 is disposed in a state where it is fixed to the subject 1 by the fixing member 9a and the positional relations with the magnetic detectors 6a to 6h similarly fixed to the subject 1 are fixed. Therefore, the inclination sensor 7 has the function of sensing the degree of inclination from the vertical direction in the xyz coordinate system constructed by the magnetic detectors 6a to 6h. The inclination sensor 7 may sense inclination only in one axis direction and, more preferably, senses inclination in the directions of two axes.

The horizontal in-plane azimuth sensor 8 is used to sense the orientation of the subject 1 in a horizontal plane. Specifically, the horizontal in-plane azimuth sensor 8 is formed by a measuring device such as a gyro and has the function of sensing the angle formed between a predetermined direction and the orientation of the subject 1. Since the horizontal in-plane azimuth sensor 8 is fixed to the subject 1 via the fixing member 9b, the azimuth angle sensed by the horizontal in-plane azimuth sensor 8 has the function of sensing an azimuth fluctuation in the horizontal direction of the xyz coordinate system constructed by the magnetic detectors 6a to 6h.

The fixing members 9a and 9b are used to fix the magnetic detectors 6a to 6h, inclination sensor 7, and horizontal in-plane azimuth sensor 8 to the subject 1. Specifically, each of the fixing members 9a and 9b is formed of, for example, an elastic member in an annular shape and is fixed in a state where it is closely attached to the trunk of the subject 1. The magnetic detectors 6a to 6d and the inclination sensor 7 are fixed to a predetermined position in the subject 1 by the fixing member 9a. The magnetic detectors 6e to 6h and the horizontal in-plane azimuth sensor 8 are fixed to a predetermined position in the subject 1 by the fixing member 9b. Therefore, by closely attaching the fixing members 9a and 9b to the trunk of the subject 1, the magnetic detectors 6a to 6h, inclination sensor 7, and horizontal in-plane azimuth sensor 8 are disposed in a state where their relative positions to the subject 1 are fixed.

Figure 3:
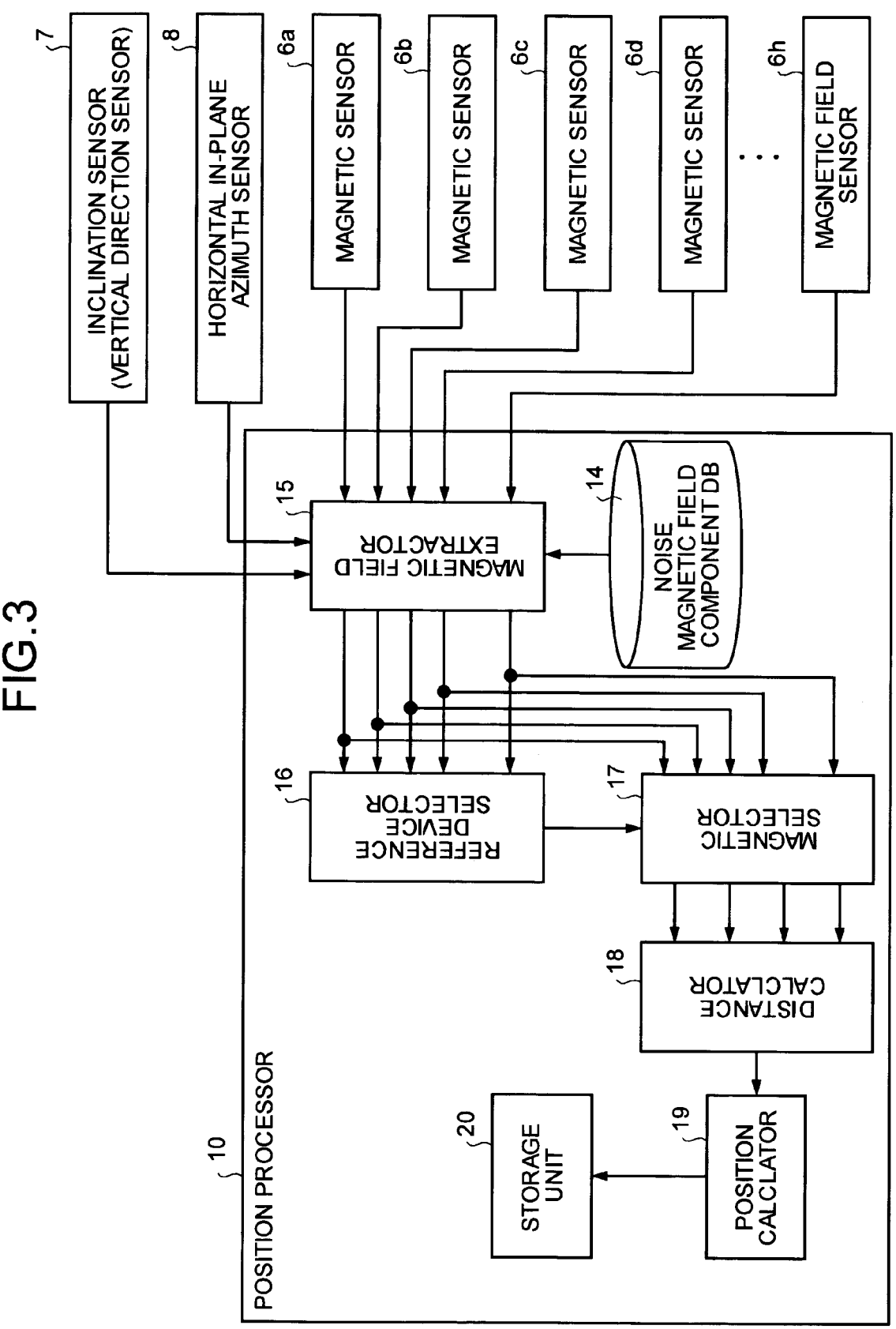
FIG. 3 is a schematic view of a position processor as a component of the system according to the first embodiment.

The position processor 10 is explained. The position processor 10 extracts intensity of the constant magnetic field output from the test capsule 2 from the magnetic field intensities sensed by the magnetic detectors 6a to 6h and, based on the extracted magnetic field intensities, calculates the position of the test capsule 2. FIG. 3 is a block diagram showing the configuration of the position processor 10. As shown in FIG. 3, the position processor 10 includes the magnetic field extractor 15 for extracting the constant magnetic field output from the test capsule 2 from the sensed magnetic fields in the magnetic detectors 6a to 6h; and a noise magnetic field component database 14 for pre-storing data used at the time of magnetic field extraction by the magnetic field extractor 15. The position processor 10 also has: a reference device selector 16 that selects a reference magnetic detector (hereinbelow, called "reference device") from the magnetic detectors 6a to 6h; a magnetic selector 17 that outputs the magnetic field intensity obtained by the predetermined number of magnetic detectors based on the result of selection by the reference device selector 16; a distance calculator 18 for calculating the distance between the test capsule 2 and the reference device or the like based on the magnetic field intensity output from the magnetic selector 17; a position calculator 19 for calculating the position of the test capsule 2 by performing a computing process using the calculated distance and position coordinates of the reference device or the like used for calculating the distance; and a storage unit 20 for storing information of the position of the test capsule 2 obtained by the position calculator 19 into the portable recording medium 5.

The noise magnetic field component database 14 stores noise magnetic fields such as earth magnetic components and the like existing in the region to which the test capsule 2 is introduced in the subject 1. Specifically, the noise magnetic field component database 14 has the function of storing the intensity of the noise magnetic field and the travel direction in the x'y'z' coordinate system and, has the function of outputting data to the magnetic field extractor 15 as necessary.

The magnetic field extractor 15 is provided to eliminate the noise magnetic field component included in the magnetic fields sensed by the magnetic detectors 6a to 6h and to extract the constant magnetic field output from the permanent magnet 12 in the test capsule 2. The magnetic field extractor 15 has a configuration of receiving not only detection results of the magnetic detectors 6a to 6h but also the information stored in the noise magnetic field component database 14 and detection results of the inclination sensor 7 and the horizontal in-plane azimuth sensor 8, and has the function of performing magnetic field extraction based on the input information. The detection results of the inclination sensor 7 and the horizontal in-plane azimuth sensor 8 are used for the following reasons.

The travel direction of the noise magnetic field component stored in the noise magnetic field component database 14 is stored based on the x'y'z' coordinate system. On the other hand, a magnetic field detected by the magnetic detectors 6a to 6h is detected based on the xyz coordinate system. Consequently, to eliminate the noise magnetic field component, the information stored in the noise magnetic field component database 14 has to be converted to information in the xyz coordinate system.

The magnetic field extractor 15 therefore derives the relation between the xyz coordinate system and the x'y'z' coordinate system at the time of detecting a magnetic field based on the results of detection by the inclination sensor 7 and the horizontal in-plane azimuth sensor 8 and, based on the derived relation between the coordinate systems, performs a process of transforming the coordinates of data of the noise magnetic field component. After the coordinate transformation process, the magnetic field extractor 15 calculates a differential value between the magnetic fields detected by the magnetic detectors 6a to 6h with respect to the x, y, and z directions and the noise magnetic field components, and outputs the calculated differential value as the constant magnetic field output from the permanent magnet 12 to the reference device selector 16 and the magnetic selector 17.

The reference device selector 16 has the function of selecting the magnetic detector with the largest value of the detected magnetic field intensity from the magnetic detectors 6a to 6h. Concretely, the reference device selector 16 compares the magnetic field intensity values output from the magnetic detectors 6a to 6h with each other, selects the magnetic detector (reference device) that has output the largest magnetic field intensity value, and outputs information specifying the reference device (for example, information indicating the reference device among the magnetic detectors 6a to 6h) to the magnetic selector 17.

The magnetic selector 17 selects a plurality of magnetic detectors based on the result of selection of the reference device selector 16 and outputs the magnetic intensities obtained by the reference device and the magnetic field intensities obtained by the selected magnetic detectors (selected devices) to the distance calculator 18. Concretely, the magnetic selector 17 has the function of selecting three magnetic detectors disposed in directions orthogonal to each other with respect to the reference device. Specifically, in the system according to the first embodiment, as also shown in FIG. 1, the magnetic detectors 6a to 6h are disposed so as to form vertexes of a cube, so that three magnetic detectors positioned in direction orthogonal to each other always exist for an arbitrary magnetic detector, and the magnetic selector 17 has the function of selecting the three magnetic detectors as selected devices.

The distance calculator 18 calculates the distances among the reference device, the selected devices, and the test capsule 2 based on the magnetic field intensities received via the magnetic selector 17. Concretely, the distance calculator 18 has the function of calculating the distance between the magnetic detector that has detected the magnetic field intensity and the test capsule 2 by performing the computing process shown by Equation (1) with respect to the input magnetic field intensity.

The position calculator 19 calculates the position of the test capsule 2 by performing a predetermined computing process based on the distance between the magnetic detector selected as a reference device or the like and the test capsule 2. The position calculator 19 also has the function of calculating the position of the test capsule 2 and, after that, outputting the result of calculation to the storage unit 20.

Figure 4:
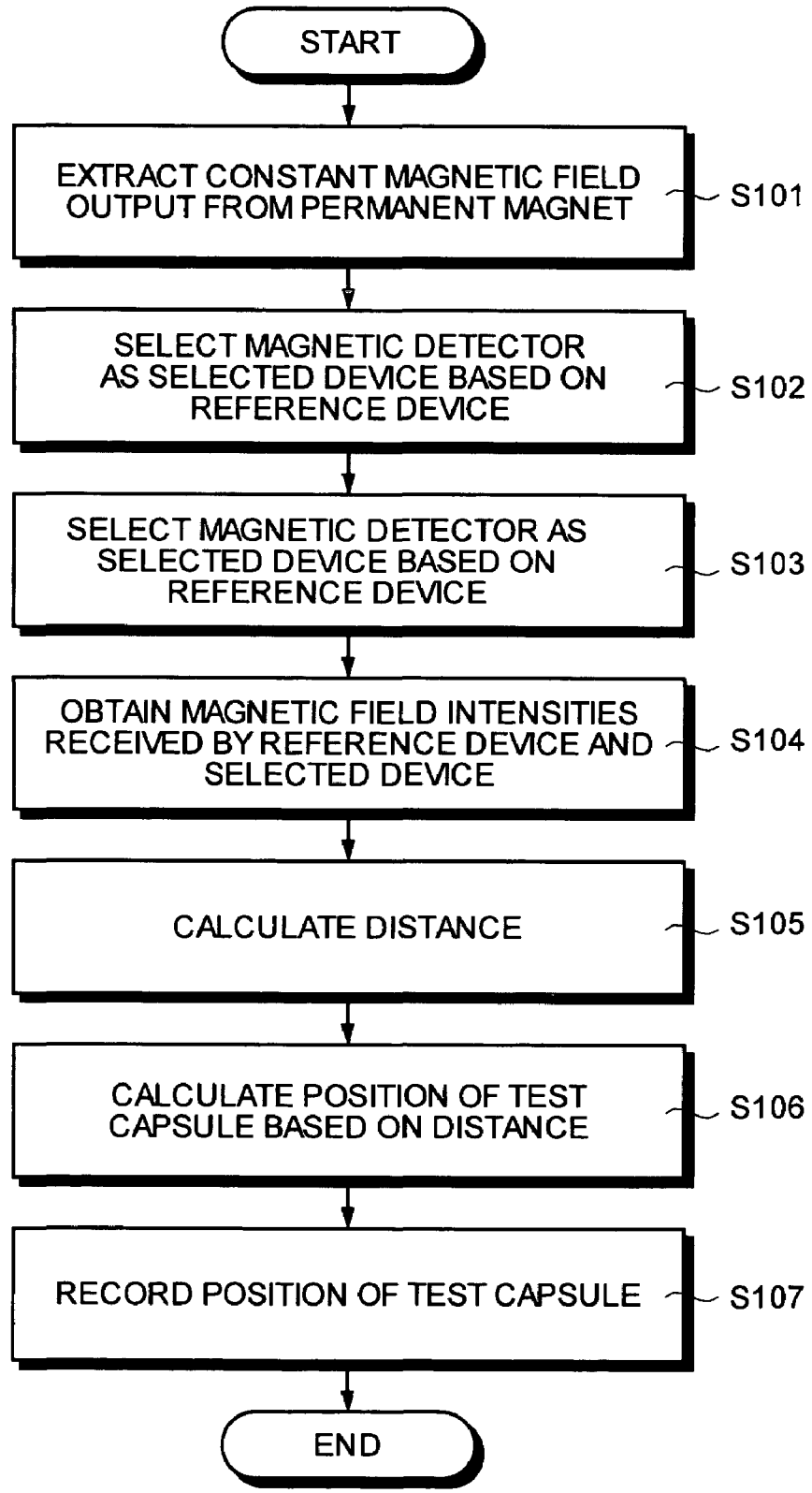
FIG. 4 is a flowchart of operations of the position processor.
Figure 5:
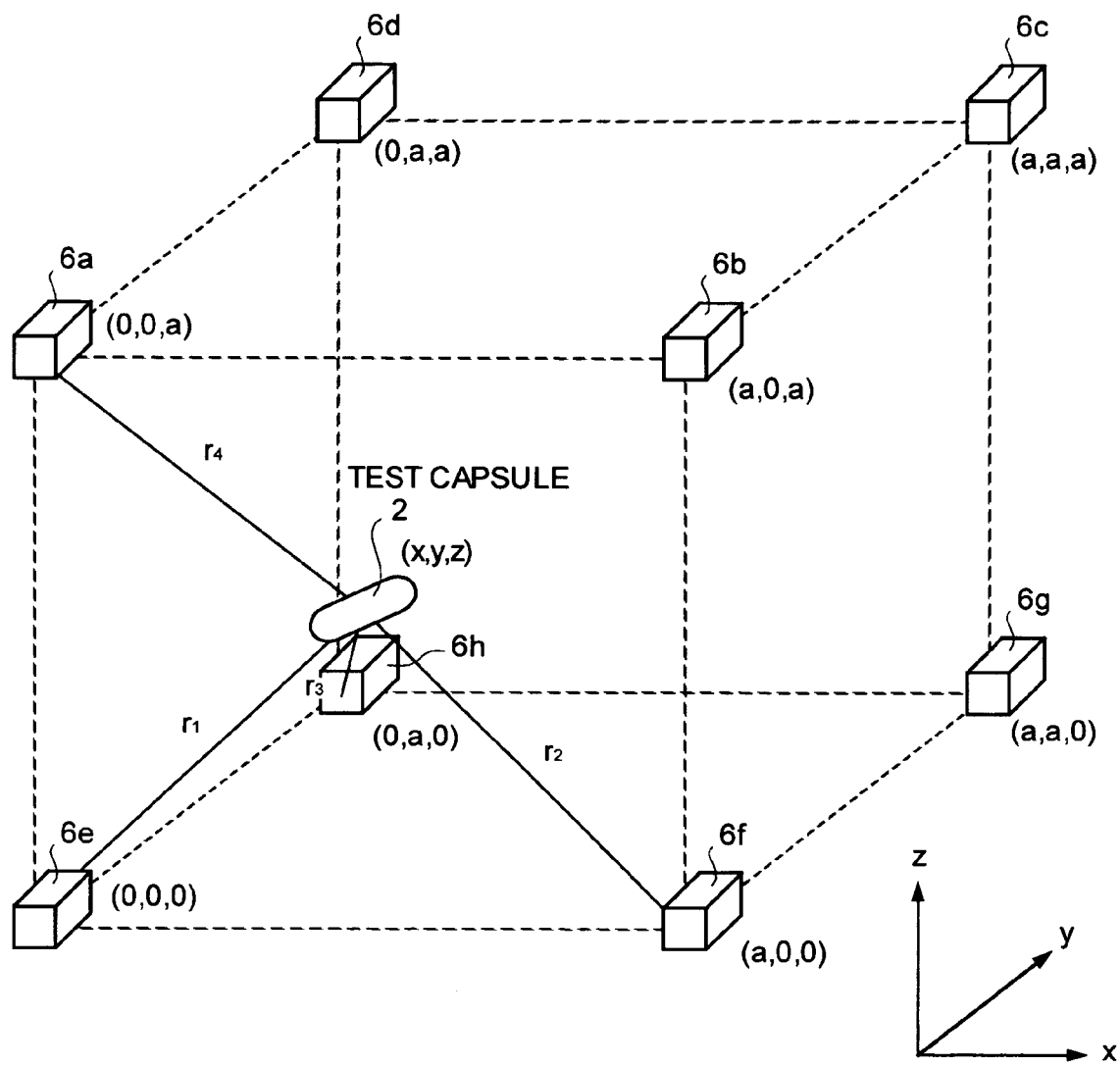
FIG. 5 is a schematic view of calculating the position of a test capsule by the position processor.

The operation of the position processor 10 in the first embodiment is explained. FIG. 4 is a flowchart that depicts the operation of the position processor 10, and FIG. 5 is a schematic diagram for explaining the algorithm of the position calculation. In FIG. 5, the length of one side of a cube constructed by the magnetic detectors 6a to 6h is set as "a". As is explained later, the position of the magnetic detector 6e selected as a reference device is set as the origin, the direction from the magnetic detector 6e toward the magnetic detector 6f is set as an x direction, the direction from the magnetic detector 6e toward the magnetic detector 6h is set as a y direction, and the direction from the magnetic detector 6e toward the magnetic detector 6a is set as a z direction. The positions of the magnetic detectors 6a to 6h are determined based on the xyz coordinate system, and the position of the test capsule 2 in the xyz coordinate system is expressed as (x,y,z). The operation of the position processor 10 is explained hereinbelow by properly referring to FIGS. 4 and 5.

First, the position processor 10 extracts the constant magnetic field output from the permanent magnet 12 from the magnetic fields detected by the magnetic detectors 6a to 6d by the magnetic field extractor 15 (step S101). Specifically, the magnetic field extractor 15 transforms information in the x'y'z' coordinate system regarding the noise magnetic field component supplied from the noise magnetic field component database 14 to information in the xyz coordinate system based on a detection result obtained by the inclination sensor 7 and the like. The magnetic field extractor 15 calculates the differential value between the noise magnetic field component subjected to the coordinate transformation and the magnetic fields detected by the magnetic detectors 6a to 6h, thereby extracting the constant magnetic field.

After that, the position processor 10 selects the magnetic detector that has detected the highest intensity of the constant magnetic field extracted by the magnetic field extractor 15 by the reference device selector 16 (step S102). The example of FIG. 5 shows a case where the magnetic detector 6e is selected as the magnetic detector that has detected the highest intensity. In the following description, it is also assumed that the magnetic detector 6e is the reference device.

The position processor 10 selects three devices by the magnetic selector 17 based on the reference device selected in step S102 (step S103), and outputs the constant magnetic field intensities detected by the selected device and the reference device and extracted by the magnetic field extractor 15 to the distance calculator 18 (step S104). In the example of FIG. 5, the magnetic detectors 6f, 6h, and 6a are disposed in the directions orthogonal to each other with respect to the magnetic detector 6e as a reference device, so that the magnetic selector 17 selects the magnetic detectors 6f, 6h, and 6a as selected devices.

After that, the position processor 10 calculates the distance from the test capsule 2 based on the constant magnetic field intensity obtained based on the detection results at the device selected at step S102 and the constant magnetic field intensities obtained based on the detection results at the devices selected in step S103 by the distance calculator 18 (step S105). Concretely, the distance calculator 18 calculates the distance by performing computation of Equation (1) using the magnetic field intensity input via the magnetic selector 17. In the example of FIG. 5, the distance calculator 18 calculates distances $r_1$, $r_2$, $r_3$, and $r_4$ between the test capsule 2 and the magnetic detectors 6e, 6f, 6h, and 6a, respectively, based on the constant magnetic field intensities obtained based on the detection results at the reference device and the selected devices.

The position processor 10 calculates the position of the test capsule 2 by the computing process in the position calculator 19 (step S106). Concretely, the position of the test capsule 2 is calculated by deriving the x coordinate, y coordinate, and z coordinate of the test capsule 2, so that the coordinates of the test capsule 2 are derived by using the coordinates of the magnetic detectors 6e, 6f, 6h, and 6a and the values of distances calculated in step S105.

For example, the position coordinates (x,y,z) of the test capsule 2 can be geometrically derived from the positional relations shown in FIG. 5 and, concretely, can be calculated by solving the following equations.

$$(x-0)^2+(y-0)^2+(z-0)^2=r_1^2 \qquad (2)$$

$$(x-a)^2+(y-0)^2+(z-0)^2=r_2^2 \qquad (3)$$

$$(x-0)^2+(y-a)^2+(z-0)^2=r_3^2 \quad (4)$$

$$(x-0)^2+(y-0)^2+(z-a)^2=r_4^2 \quad (5)$$

In Equations (2) to (5), the number of unknown letters is three so that three equations are theoretically sufficient. At the time of actual position detection, however, to suppress deterioration in precision of the position detection of the test capsule 2 due to positional deviations of the magnetic detectors 6a to 6h, a distance derivation error, and the like, after solving Equations (2) to (5), the coordinates of the magnetic detector, and the like are corrected so that the values x, y, and z are unconditionally determined.

Finally, the position processor 10 stores the position of the test capsule 2 calculated in step S106 by the storage unit 20 (step S107). Concretely, while the test capsule 2 is swallowed in the subject 1, the portable recording medium 5 is inserted in the storage unit 20, so that the storage unit 20 records the position information obtained in step S106 into the portable recording medium 5.

The processes in steps S102 to S107 are repeatedly performed at predetermined time intervals. As a result, the portable recording medium 5 records information of travel in the subject 1 of the test capsule 2. After the test capsule 2 is excreted to the outside of the subject 1, the portable recording medium 5 is inserted to the display 4. The user grasps how the test capsule 2 travels in the subject 1 based on the result of recording displayed on the display 4 and determines the location of a narrow region existing in the subject 1 or the like from the grasped result.

The advantages of the system according to the first embodiment is explained. First, the system according to the first embodiment calculates the position of the test capsule 2 based on the constant magnetic field output from the permanent magnet 12 in the test capsule 2. Different from electromagnetic waves and the like, the constant magnetic field has a characteristic that its intensity attenuates almost unconditionally irrespective of physical parameters such as dielectric constant, magnetic permeability, and the like in a propagation region, so that the relation of Equation (1) is excellently satisfied. Therefore, the system has an advantage such that position detection can be performed with higher precision even in a space like the inside of a human body where organs and the like whose physical parameters are different from each other exist as compared with position detection using electromagnetic waves or the like.

Another advantage of using the constant magnetic field is that burden on the subject when the test capsule 2 is introduced into the subject 1 is lessened. For the above reasons, the system according to the first embodiment has an advantage such that deterioration in precision of the position detection due to variations of environments around the test capsule 2 is suppressed. Consequently, for example, at the time of introducing the test capsule 2 into the subject 1, it is unnecessary to impose limitations such as restriction on eating and drinking like in other inspecting methods. Therefore, the subject 1 can live normal life also at the time of an inspection using the test capsule 2 and the burden on the subject 1 in the inspection can be lessened.

A modification of the system for detecting a position in a subject according to the first embodiment is explained. In the modification, the arrangement of the permanent magnet 12 is devised so that the constant magnetic field output from the test capsule is always in the vertical direction.

Figure 6:
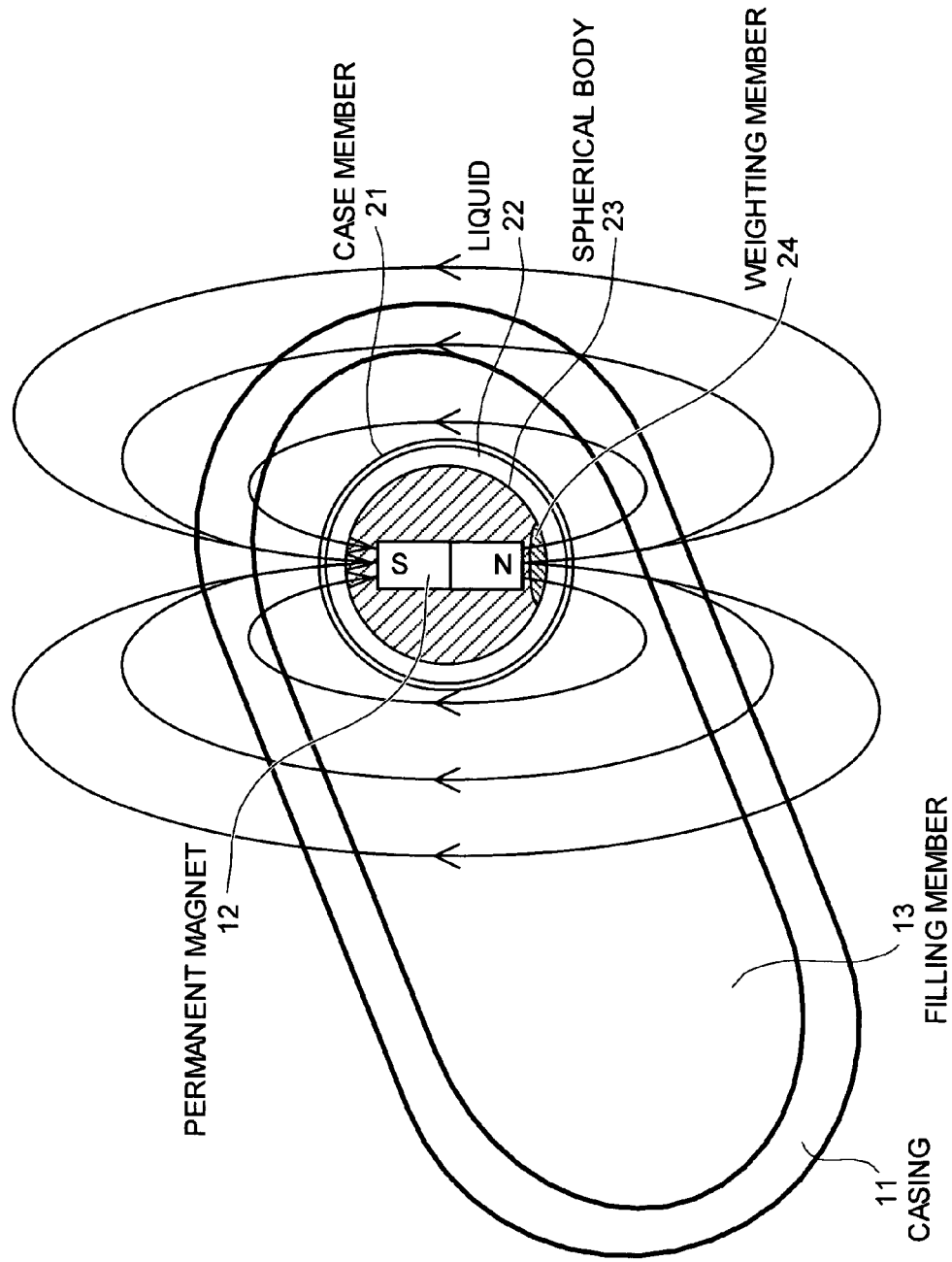
FIG. 6 is a schematic view of the test capsule according to a modification of the first embodiment.

FIG. 6 is a schematic view that depicts the configuration of a test capsule according to the modification. As shown in FIG. 6, the test capsule in the modification has the casing 11 and the filling member 13 in a manner similar to the first embodiment and the permanent magnet 12 is housed in a case member 21. Specifically, the permanent magnet 12 is held in a spherical body 23 and the spherical body 23 is disposed in a state where it floats in a liquid 22 held in the case member 21. In the spherical body 23, a weighting member 24 is disposed in the magnetic field output direction from the permanent magnet 12. The spherical body 23 is stabilized in a state where the weighting member 24 is positioned at the bottom in the vertical direction irrespective of fluctuations in the orientation of the test capsule as shown in FIG. 6.

With the configuration, in the modification, the constant magnetic field output from the permanent magnet 12 in the test capsule is always in the vertical direction. On the other hand, the earth magnetic component as a main noise magnetic field component travels almost in the horizontal direction, so that it is sufficient for the magnetic field extractor 15 to extract only the components in the vertical direction from the magnetic fields detected by the magnetic detectors 6a to 6h.

To extract the components in the vertical direction from the detected magnetic fields, the magnetic field extractor 15 extracts only the components parallel to the vertical direction sensed by the inclination sensor 7 from the magnetic fields detected by the magnetic detectors 6a to 6h, thereby enabling extraction of the constant magnetic field output from the permanent magnet 12 to be completed. Therefore, in the modification, the position transducer 3 does not have to have the horizontal in-plane azimuth sensor 8, and the noise magnetic field component database 14 can be omitted from the position processor 10. Further, in the modification, the magnetic field extractor 15 does not have to perform a process of deriving a differential value and the like. Thus, by using the test capsule shown in FIG. 6, a system for detecting a position in a subject, in which the influence of noise magnetic field components is reduced can be realized with a simple configuration.

A system for detecting a position of a capsule endoscope in a subject according to a second embodiment will now be explained. The system according to the second embodiment includes a capsule endoscope, as a device swallowed and passing through a subject, including not only the constant magnetic field generator but also a predetermined function executing unit and a radio unit; and a position processor for switching a plurality of antennas for receiving radio signals transmitted from the capsule endoscope based on the constant magnetic field generated by constant magnetic field generator and the result of detection of the position of the capsule endoscope in the subject as well as the direction of the longitudinal axis of the capsule endoscope having a shape of spheroid, in other words, the orientation direction of the capsule endoscope.

Figure 7:
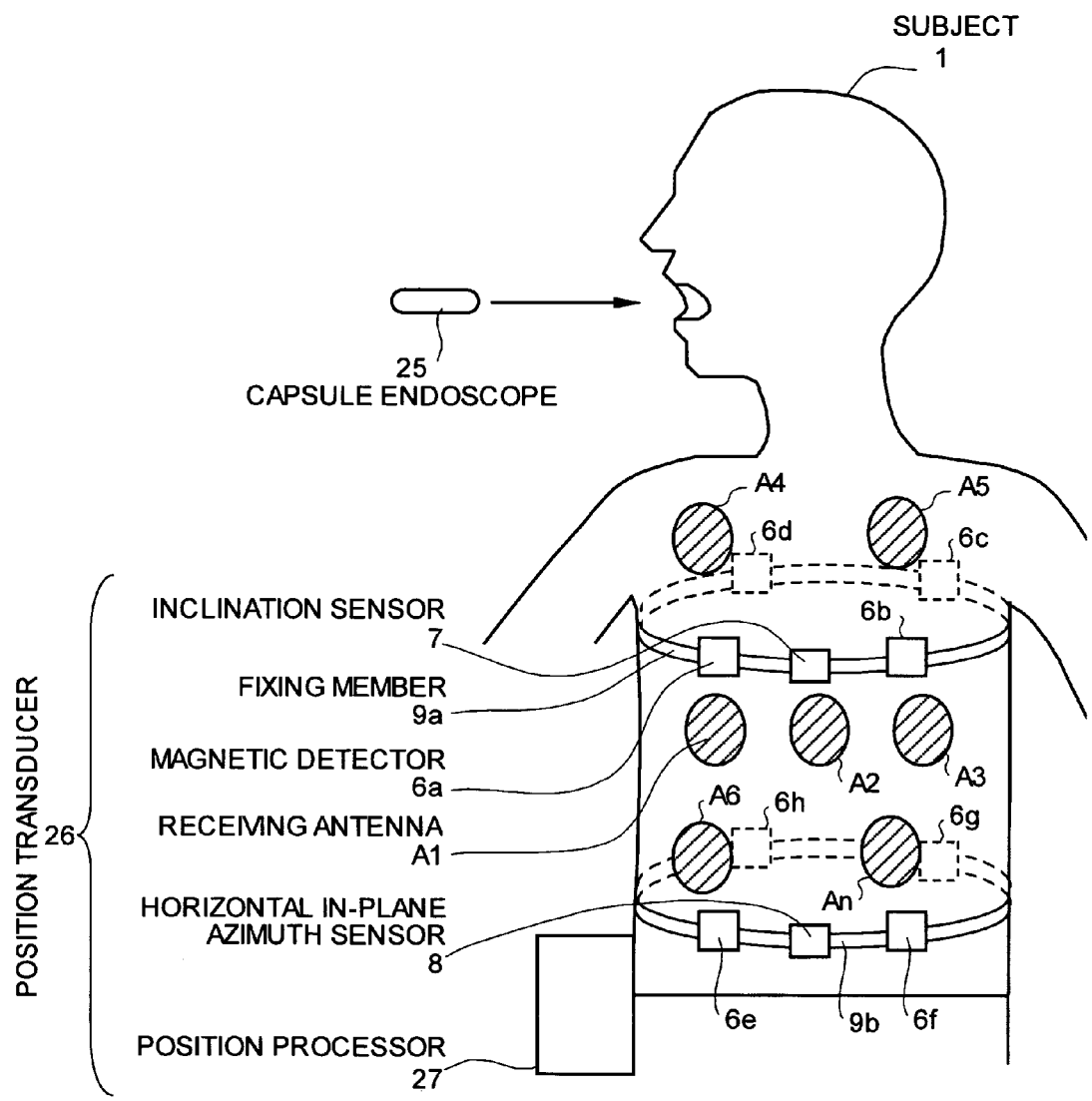
FIG. 7 is a schematic view of a system for detecting a position of a capsule endoscope in a subject according to a second embodiment.

FIG. 7 is a schematic diagram of the system according to the second embodiment. As shown in FIG. 7, the system according to the second embodiment includes a capsule endoscope 25 as an example of the device to be swallowed and passes through a subject, and a position transducer 26. Although elements corresponding to the display 4 and the portable recording medium 5 in the first embodiment are not shown in FIG. 7, it does not mean that those elements are excluded in the second embodiment. In the system according to the second embodiment, elements having the same reference numerals and names as those of the first embodiment have the same configurations and actions as those of the first embodiment unless otherwise specified in the following.

The position transducer 26 includes, as shown in FIG. 7, the magnetic detectors 6a to 6h, the inclination sensor 7, the horizontal in-plane azimuth sensor 8, the fixing members 9a and 9b for fixing the magnetic detectors 6a to 6h to the subject 1, receiving antennas $A_1$ to $A_n$ for receiving radio signals transmitted from the capsule endoscope 25, and a position processor 27 for processing the information obtained by the magnetic detector 6a to 6h and the receiving antennas $A_1$ to $A_n$ and deriving information of the position in the subject 1, of the capsule endoscope 25. Though not described in FIG. 7, the position transducer 26 also includes the power supply antennas $B_1$ to $B_m$.

The receiving antennas $A_1$ to $A_n$ are to receive radio signals transmitted from the capsule endoscope 25. As is explained later, the capsule endoscope 25 in the second embodiment has the function of capturing an image of the inside of the subject 1 and transmitting the image to the outside by radio. The receiving antennas $A_1$ to $A_n$ have the configuration of receiving a radio signal transmitted from the capsule endoscope 25 and outputting it to the position processor 27. The receiving antennas $A_1$ to $A_n$ are constructed by, concretely, for example, a loop antenna and a fixing unit that fixes the loop antenna to the subject 1. When radio signals are transmitted from the capsule endoscope 25, the radio signals may be received by all of the receiving antennas $A_1$ to $A_n$. However, in the second embodiment, the radio signal is received by using a receiving antenna that is determined to be most adapted to reception by an antenna selector 46 that is explained later among the plurality of receiving antennas $A_1$ to $A_n$.

The capsule endoscope 25 includes, like the test capsule 2 in the first embodiment, the permanent magnet 12 as the magnetic field generator. The capsule endoscope 25 also includes the function of a function executing unit for executing a predetermined function on the inside of the subject 1 and the function of a receiver for receiving a radio signal transmitted from the position transducer 26, and has components corresponding to the functions.

Figure 8:
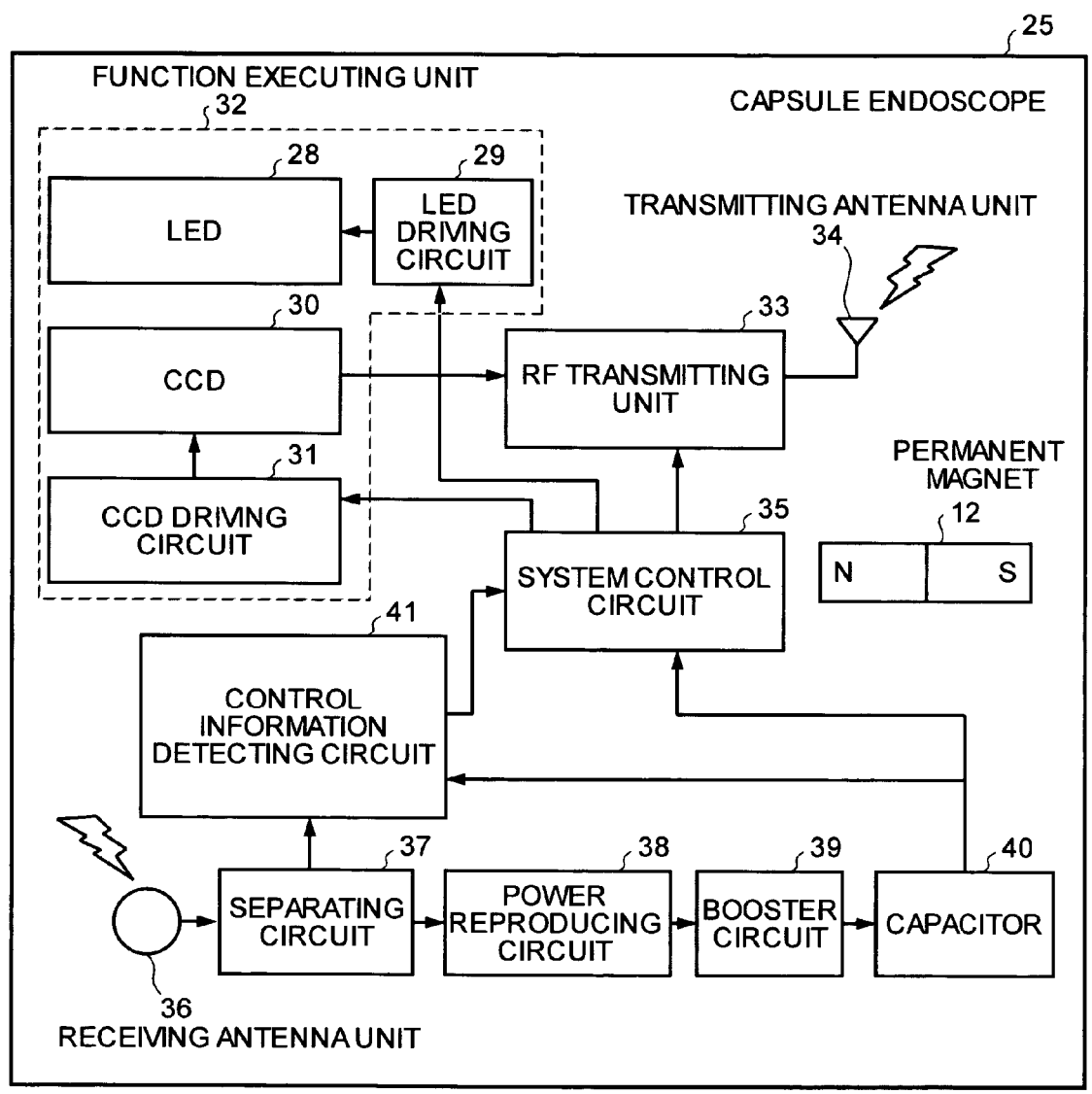
FIG. 8 is a schematic view of the capsule endoscope as a component of the system according to the second embodiment.

First, the capsule endoscope 25 has a configuration to realize the function as a function executing unit for executing a predetermined function and as a transmitting unit for radio transmitting information obtained by the function executing unit. FIG. 8 is a block diagram of the capsule endoscope 25. Specifically, the capsule endoscope 25 includes a light emitting diode (LED) 28 functioning as a illuminating unit that illuminates an image capturing region at the time of capturing an image of the inside of the subject 1; an LED driving circuit 29 that controls a driving state of the LED 28; a charge-coupled device (CCD) 30 functioning as an image capturing unit for capturing a reflection light image from the region illuminated by the LED 28; and a CCD driving circuit 31 that controls a driving state of the CCD 30. The LED 28, LED driving circuit 29, CCD 30, and CCD driving circuit 31 are defined as a function executing unit 32 having a predetermined function as a whole.

The capsule endoscope 25 includes an RF transmitting unit 33 that modulates image data captured by the CCD 30, thereby generating an RF signal; a transmitting antenna unit 34 as a radio unit for transmitting the RF signal output from the RF transmitting unit 33 by radio; and a system control circuit 35 for controlling the operation of the LED driving circuit 29, CCD driving circuit 31, and RF transmitting unit 33.

By having the mechanisms, the capsule endoscope 25 obtains image data of a region to be tested that is illuminated by the LED 28 by the CCD 30 while the capsule endoscope 21 is introduced in the subject 1. The captured image data is converted to an RF signal by the RF transmitting unit 33 and, after that, the RF signal is transmitted to the outside via the transmitting antenna unit 34.

The capsule endoscope 25 also has a configuration to receive radio signals transmitted from the position transducer 26. Specifically, the capsule endoscope 25 includes a receiving antenna unit 36 for receiving a radio signal sent from the position transducer 26 side; and a separating circuit 37 for separating the power supply signal from the signal received by the receiving antenna unit 36. The capsule endoscope 25 also includes a power reproducing circuit 38 for reproducing power from the separated power supply signal; a booster circuit 39 for boosting the reproduced power; and a capacitor 40 for storing the boosted power. The capsule endoscope 25 also includes a control information detecting circuit 41 for detecting a control information signal from the components separated from the power supply signal by the separating circuit 37 and outputting the detected control information signal to the system control circuit 35. The system control circuit 35 also includes the function of distributing drive power supplied from the capacitor 40 to the other elements.

By having the mechanisms, first, the capsule endoscope 25 receives the radio signal sent from the position transducer 26 side by the receiving antenna unit 36 and separates the power supply signal and the control information signal from the received radio signal by the separating circuit 37. The control information signal separated by the separating circuit 37 is output to the system control circuit 35 via the control information detecting circuit 41 and used for driving and controlling the LED 28, CCD 30, and RF transmitting unit 33. On the other hand, the power supply signal is reproduced as power by the power reproducing circuit 38. The potential of the reproduced power is boosted to potential adapted to the capacitor 40 by the booster circuit 39, and the boosted potential is stored in the capacitor 40.

Figure 9:
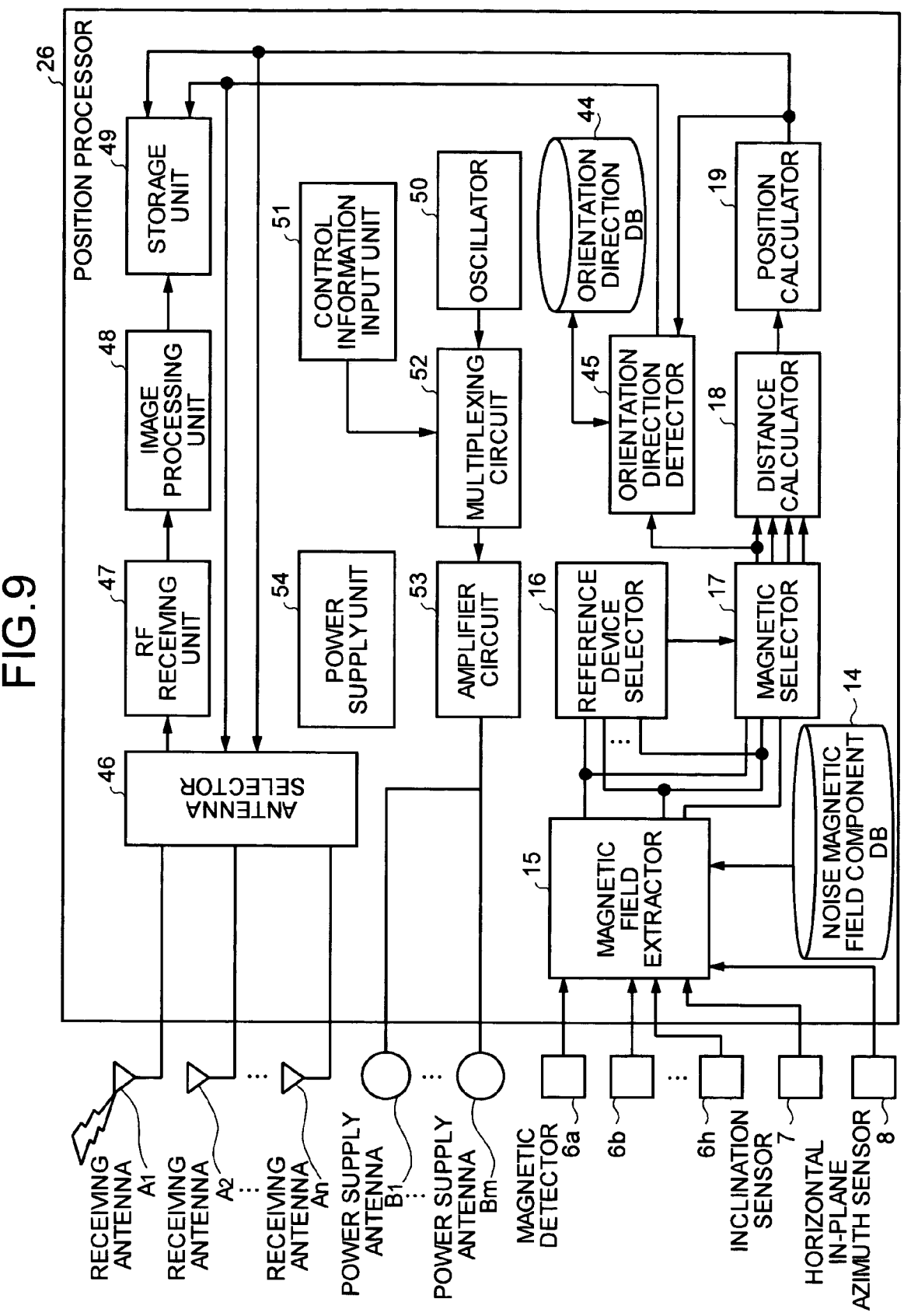
FIG. 9 is a schematic view of a position processor as a component of the system according to the second embodiment.

The configuration of the position processor 27 is explained. The position processor 27 has not only the function of deriving the position of the capsule endoscope 25 but also the function of deriving the orientation and, further, has the function of a receiver for receiving a radio signal transmitted from the capsule endoscope 25 and the function of a transmitter for transmitting a predetermined signal by radio to the capsule endoscope 25. The configuration of the position processor 27 is explained below with respect to each of the components corresponding to the functions. FIG. 9 is a block diagram of the position processor 27. The position processor 27 in the second embodiment has, as elements for detecting the position in the subject 1 of the capsule endoscope 25, the noise magnetic field component data base 14, the magnetic field extractor 15, the reference device selector 16, the magnetic selector 17, the distance calculator 18, and the position calculator 19. In the second embodiment, the magnetic detectors 6a to 6h output not only the magnetic field intensity but also the magnetic field direction to the position processor 27, so that the second embodiment is different from the first embodiment with respect to the following points. The reference device selector 16 extracts the magnetic field intensity from the information output from the magnetic detectors 6a to 6h to select a reference device, and the distance calculator 18 has the function of deriving distance by extracting the magnetic field intensities received by the reference device and the selected devices from the information input from the magnetic selector 17. The operation of detecting the position of the capsule endoscope 25 in the second embodiment is almost the same as that in the first embodiment and its detailed description will not be repeated.

Furthermore, the position processor 27 includes an orientation direction database 44 used when detecting the orientation direction of the capsule endoscope 25 as described below, and an orientation direction detector 45 that detects the orientation direction of the capsule endoscope 25 based on the magnetic field direction at a predetermined magnetic detector 6 output from the magnetic selector 17. The orientation direction database 44 stores in advance data on magnetic field intensity received at the magnetic detector 6 and orientation directions relative to the positional relationship between the magnetic detectors 6 and the capsule endoscope 25. The specific operation of the orientation direction database 44 and orientation direction detector 45 will be described later in detail.

The position processor 27 also has a configuration as a receiving apparatus for receiving image data of the inside of the subject 1, which is sent from the capsule endoscope 25 by radio. Concretely, the position processor 27 includes the antenna selector 46 for selecting an antenna used for data reception from the receiving antennas $A_1$ to $A_n$; an RF receiving unit 47 that performs a predetermined process such as demodulation on a radio signal received by the selected receiving antenna, extracts image data captured by the capsule endoscope 25 from the radio signal, and outputs the extracted image data; an image processing unit 48 for performing a necessary process on the output image data; and a storage unit 49 for storing the processed image data.

The antenna selector 46 selects the receiving antenna that is most adapted to receive the radio signal transmitted from the capsule endoscope 25. Concretely, the antenna selector 46 grasps the positions of the receiving antennas $A_1$ to $A_n$ in advance and receives information of the position of the capsule endoscope 25 calculated by the position calculator 19 and information of the orientation direction of the capsule endoscope 25 derived by the orientation direction detector 45. The antenna selector 46 has the function of selecting a receiving antenna that is estimated to have the most excellent reception sensitivity based on the position and the orientation direction of the capsule endoscope 25 and outputting a radio signal received by the selected receiving antenna to the RF receiving unit 47.

The storage unit 49 has the function of storing image data output from the image processing unit 48 and the position and the orientation direction of the capsule endoscope 25 at the time point the output image data is captured in a state where the image data and the position of the capsule endoscope 25 are associated with each other. The position processor 27 has the configuration of outputting the information obtained by the position calculator 19, orientation direction detector 45, and the image processing unit 48 to the storage unit 49 as also shown in FIG. 9, and the storage unit 49 has the function of storing the information in the associated state. As a result, in the storage unit 49, the image data of a predetermined region in the subject 1 and the position and the orientation direction of the capsule endoscope 25 at the time point the image data is captured is stored in a state where the image data and the position and the orientation direction of the capsule endoscope 25 are associated with each other.

The position processor 27 also has the function of generating a power supply signal and the like transmitted to the capsule endoscope 25 and outputting the power supply signal to the power supply antennas $B_1$ to $B_m$. Concretely, the position processor 27 includes an oscillator 50 having the function of generating a power supply signal and the function of specifying an oscillation frequency; a control information input unit 51 that generates a control information signal for controlling the drive state of the capsule endoscope 25; a multiplexing circuit 52 for combining the power supply signal and the control information signal; and an amplifier circuit 53 for amplifying the intensity of the combined signal. The signal amplified by the amplifier circuit 53 is sent to the power supply antennas $B_1$ to $B_m$ and transmitted to the capsule endoscope 25. The position processor 27 includes a power supply unit 54 having a predetermined storage, an AC power adapter, or the like, and the elements of the position processor 27 uses the power supplied from the power supply unit 54 as driving energy.

Next, in the system for detecting a position within a subject according to the second embodiment, the significance of detection of the orientation direction of the capsule endoscope 25 and the operation of detecting the orientation direction will be described. As described above, in the system for detecting a position in a subject according to the second embodiment, the capsule endoscope 25 includes a predetermined function executing unit and the information acquired by the function executing unit is wirelessly transmitted to the position transducer 26 side. Accordingly, the position transducer 26 includes plural receiving antennas $A_1$ to $A_n$ for receiving transmitted radio signals and antenna selector 46 selects a receiving antenna most suitable for reception from the plural receiving antennas $A_1$ to $A_n$.

As an algorithm of selecting a receiving antenna most suitable for reception from the plural receiving antennas $A_1$ to $A_n$, first, determination according to the positional relationship with the capsule endoscope 25 can be cited. For example, it is conceivable that, on the assumption that the radio signal transmitted from the capsule endoscope 25 are attenuated according to the distance, the position of the capsule endoscope 25 is calculated by a position detection mechanism same as in the first embodiment, and the receiving antenna nearest to the calculated position is used.

However, when the radio signals from the capsule endoscope are received, selecting the receiving antenna according to only the positional relationship with the antenna is not necessarily appropriate. That is, the transmitting antenna unit 34 used for radio transmission from the capsule endoscope 25 does not transmit the radio signals toward various directions with uniform intensity, but transmits the radio signals with a certain degree of directivity because the unit is formed by a loop antenna or the like, for example. Therefore, it is preferred that the receiving antenna most suitable for receiving the radio signals transmitted from the capsule endoscope is not determined according to only the positional relationship with the capsule endoscope, but determined in consideration of the directivity of the radio signals transmitted from the transmitting antenna unit 34. Further, since the transmitting antenna unit 34 is fixed within the capsule endoscope 25, it is important to grasp the orientation direction of the capsule endoscope 25 within the subject 1 to detect the orientation direction of the transmitted radio signals. According to such circumstances, in the second embodiment, the orientation direction of the capsule endoscope 25 is detected with not only the mechanism of detecting the position of the capsule endoscope 25 within the subject 1 as in the first embodiment, but with the orientation direction database 44 and the orientation direction detector 45.

Figure 10:
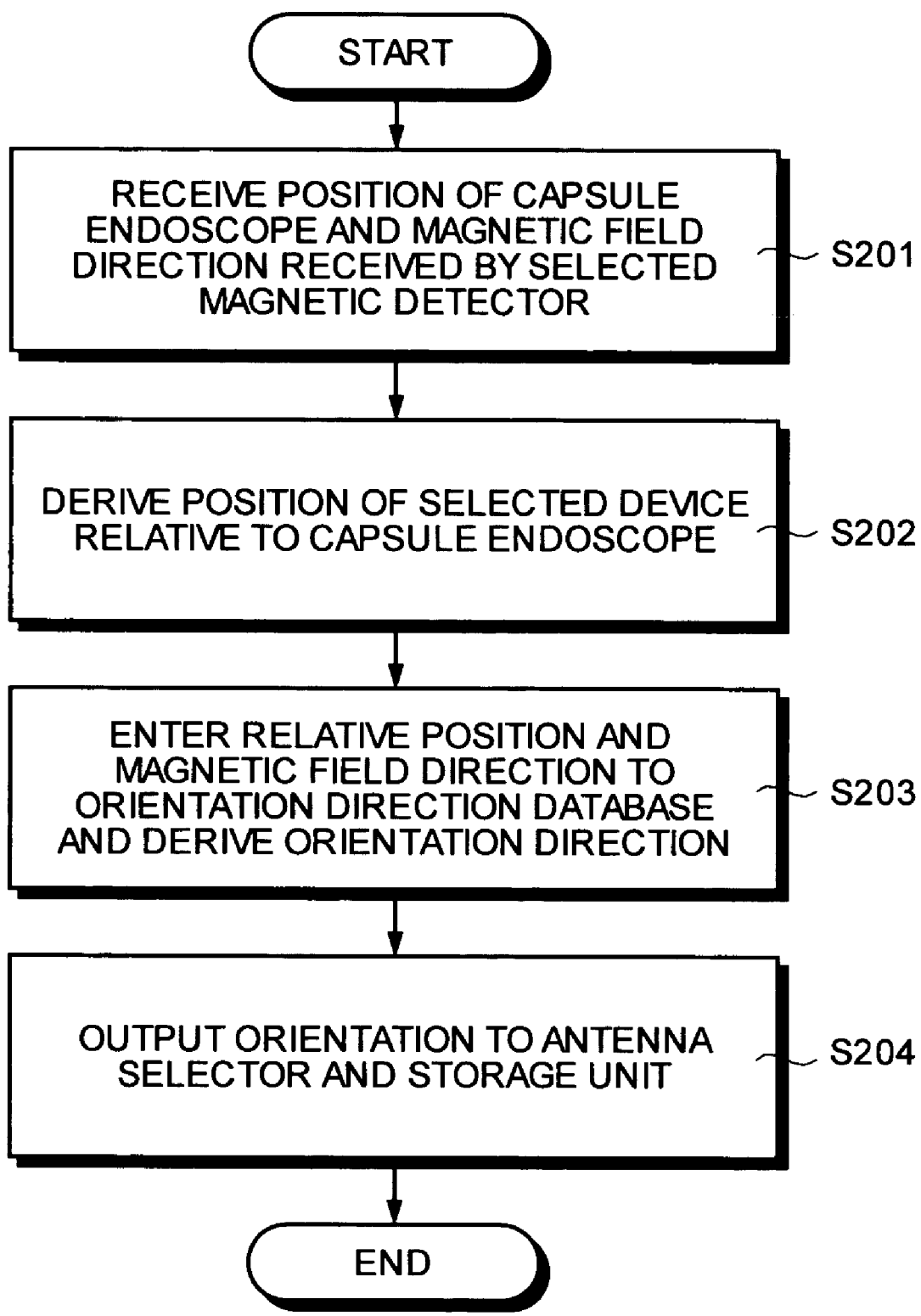
FIG. 10 is a flowchart of operations of the position processor.
Figure 11:
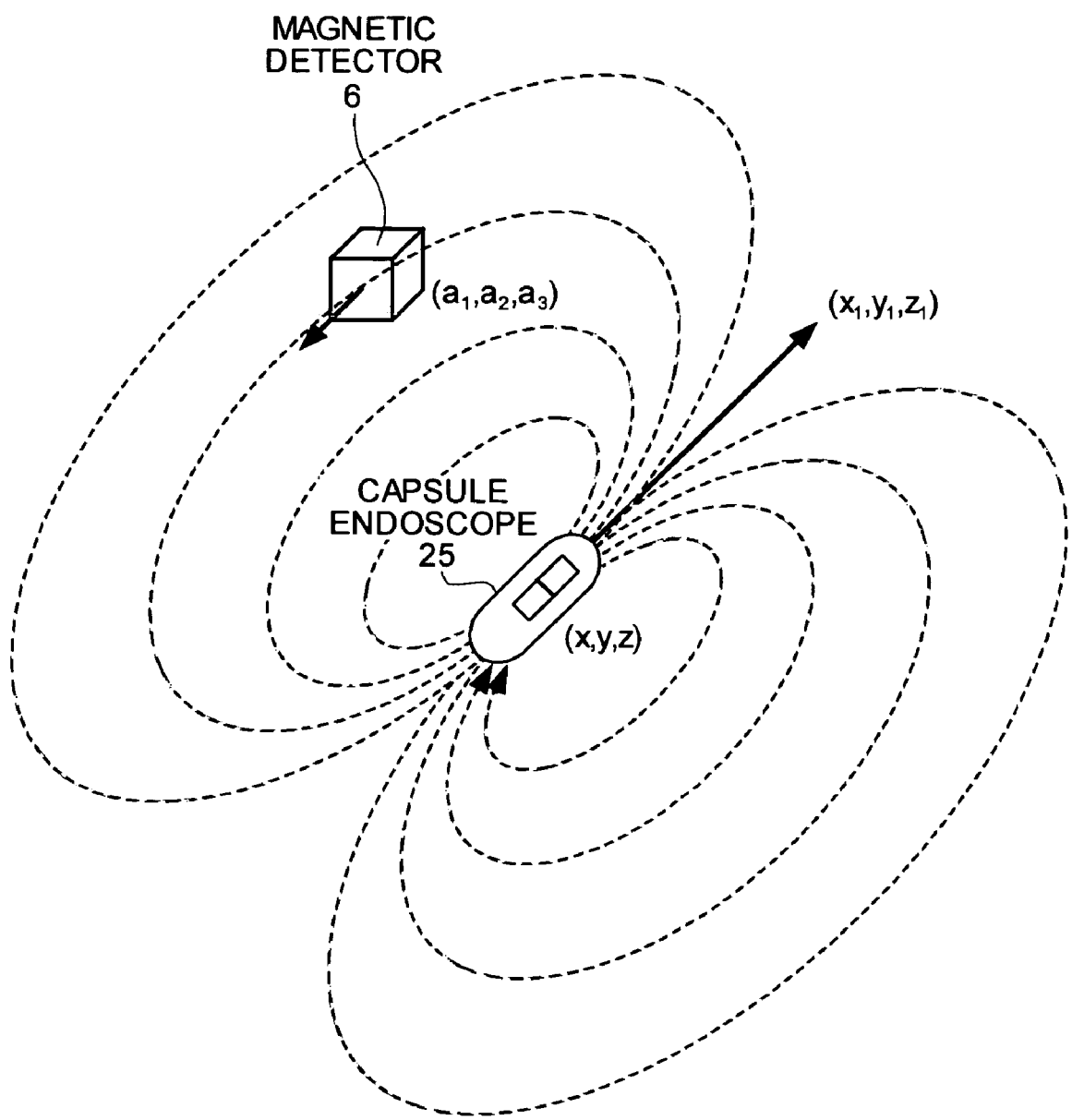
FIG. 11 is a schematic view of calculating the orientation direction of the test capsule by the position processor.

FIG. 10 is a flowchart for explanation of the detection operation of the orientation direction of the capsule endoscope 25 in the orientation direction detector 45 in the second embodiment. Further, FIG. 11 is a diagram that depicts the relationship between the orientation direction of the capsule endoscope and the magnetic detector 6. As below, the operation of the orientation direction detector 45 will be described with reference to FIGS. 10 and 11 as necessary.

First, the orientation direction detector 45 inputs the position of the capsule endoscope 25 and magnetic field direction of the constant magnetic field detected by the magnetic detector 6 selected from the magnetic detectors 6a to 6h and extracted by the magnetic field extractor 15 (step S201). Any selection algorithm may be used for the selection of the magnetic detector 6, and in the second embodiment, the magnetic detector 6 with the largest received magnetic field intensity is selected as an example. In the example of FIG. 11, the orientation direction detector 45 grasps the coordinates $(a_1, a_2, a_3)$ of the selected magnetic detector 6 and the magnetic field direction represented by the direction vector shown by an arrow.

Then, the orientation direction detector 45 calculates the relative position of the magnetic detector 6 selected at step S201 to the capsule endoscope 25 (step S202). Specifically, the position of the capsule endoscope 25 calculated by the position calculator 19 is input to the orientation direction detector 45, and the unit 45 derives the relative coordinates of the magnetic detector 6 selected at step S201 to the capsule endoscope 25. In the example of FIG. 11, the relative position coordinates $(a_1\text{-}x, a_2\text{-}y, a_3\text{-}z)$ of the magnetic detector 6 with the position of the capsule endoscope 25 as a point of origin are calculated based on the coordinates $(a_1, a_2, a_3)$ of the magnetic detector 6 and the coordinates (x,y,z) of the capsule endoscope 25.

Then, the orientation direction detector 45 inputs the magnetic field direction input at step S201 and the relative position of the magnetic detector 6 selected at step S202 to the orientation direction database 44 and acquires data on the orientation direction of the capsule endoscope 25 (step S203). As shown in FIG. 11, since the direction of the constant magnetic field output from the permanent magnet 12 provided within the capsule endoscope 25 has a nature which is uniquely determined depending on the orientation direction of the capsule endoscope 25 and the position relative to the capsule endoscope 25, in the orientation direction database 44, the orientation direction of the capsule endoscope 25, the relative coordinates to the capsule endoscope 25, and the directions of the constant magnetic field in the relative coordinates are stored in advance in an associated condition. Accordingly, with the input of the relative coordinates of the magnetic detector 6 and the detected direction of the constant magnetic field to the orientation direction database 44, the orientation direction of the capsule endoscope 25 can be extracted. In the example in FIG. 11, the orientation direction of the capsule endoscope 25 is derived as $(x_1, y_1, z_1)$ based on the output result from the orientation direction database 44.

Finally, the orientation direction detector 45 outputs the acquired data on the orientation direction of the capsule endoscope 25 to the antenna selector 46 and the storage unit 49 (step S204). The antenna selector 46 selects the receiving antenna most suitable for reception based on the data on the orientation direction and the information on the position output from the position calculator 19, and the storage unit 49 stores the orientation direction of the capsule endoscope 25 at a predetermined time in association with the image data and the position information of the capsule endoscope 25.

The advantages of the system according to the second embodiment is explained. First, in the system according to the second embodiment, in a manner similar to the first embodiment, the capsule endoscope 25 includes therein the permanent magnet 12 and the position of the capsule endoscope 25 is detected through the extraction of the constant magnetic field output from the permanent magnet 12 from the detected magnetic field and based on the thus extracted constant magnetic field. As already mentioned above, the constant magnetic field has a characteristic that it attenuates almost unconditionally irrespective of the values such as dielectric constant, magnetic permeability, and the like in organs and the like in the subject 1. Consequently, there is an advantage such that the position of the capsule endoscope 25 can be accurately detected more than the case of performing position detection by using a radio signal.

Further, the system according to the second embodiment has a configuration that the orientation direction of the capsule endoscope 25 is detected based on the constant magnetic field output from the permanent magnet 12. Similarly to the position detection, the constant magnetic field output from the permanent magnet 12 is hardly affected by the component material within the subject 1 and has a property that the magnetic field direction in the predetermined position is nearly uniquely determined based on the orientation direction of the capsule endoscope 25 and the relative position to the capsule endoscope 25. Therefore, when the distribution of orientation of the constant magnetic field output by the permanent magnet 12 is obtained in advance to be stored in the orientation direction database 44, with the reference to the orientation direction database 44 based on the information obtained via magnetic detector 6, the orientation direction of the capsule endoscope 25 can be detected accurately.

Furthermore, since the system according to the second embodiment has the configuration that the orientation direction of the capsule endoscope 25 is detected based on the constant magnetic field similarly to the position detection, the system has an advantage of simple configuration. That is, the system according to the second embodiment does not require addition of new components within the capsule endoscope 25 for realizing the function of detecting the orientation direction of the capsule endoscope 25, whereby the compact and low-cost system can be realized.

The system for detecting a position in a subject according to the second embodiment has a configuration that the antenna selector 46 selects the receiving antenna based on the position and the orientation direction of the capsule endoscope 25. The reception sensitivity of the radio signal in the receiving antenna depends on the distance from the capsule endoscope 25 and the orientation of the transmitting antenna unit 34 in the capsule endoscope 25. Therefore, a receiving antenna to be used can be accurately selected based on the position and the orientation direction of the capsule endoscope 25, and a position information detecting system capable of receiving a radio signal transmitted from the capsule endoscope 25 always at high sensitivity can be realized.

Further, the system according to the second embodiment has a configuration of outputting image data of the inside of the subject 1 captured and the calculated position and the orientation direction of the capsule endoscope 25 to the storage unit 49. Therefore, image data obtained by the capsule endoscope 25 and the calculated position and the orientation direction at the time of image capture of the capsule endoscope 25 can be stored so as to be associated with each other. At the time of displaying image data on the display 4, only the image data positioned in a predetermined range can be designated to be displayed. In other words, every image data is not displayed on the display 4 but image data of a region of interest of the user, for example, image data of only the small intestine can be displayed on the display 4. Thus, the position information detecting system that is convenient to doctors and the like can be realized.

Although the invention has been described above by the first and second embodiments, the invention is not limited to the foregoing embodiments and various embodiments, modifications, and application examples can be made by those skilled in the art. For example, the system according to the first embodiment may have a configuration where the orientation direction of the test capsule 2 is derived as in the second embodiment and the configuration of the test capsule according to the modification of the first embodiment may be applied for the capsule endoscope 25 according to the second embodiment.

Further, though in the first and the second embodiments, a plurality of magnetic detectors 6 are each disposed on an outer surface of the subject 1 as to detect an apex of the cube, the disposition of the detectors is not limited to such. With respect to the magnetic detectors 6 and the like, it is sufficient to grasp relative positions to the subject 1 in advance. By using the relative positions, position and orientation direction detection is possible without disposing the magnetic detectors 6 in a cube shape. The number of the magnetic detectors 6 and the like is not limited to eight. As the simplest configuration, a system using a single magnetic detector 6 or the like can be constructed. Specifically, the test capsule 2 or the capsule endoscope 25 as the device to be introduced in the subject does not travel arbitrarily in the subject 1 but travels along a path that is determined to a certain degree of predetermined organs such as esophagus, stomach, small intestine, large intestine, and the like. Therefore, it is possible to preliminarily grasp a travel path of the device to be introduced in a subject to a certain degree. The position of the device to be introduced in a subject can be detected by using the path information grasped in advance and the intensity of the constant magnetic field received by the single magnetic detector.

Further, in the first and second embodiments, the reference device and the selected devices are selected by using the reference device selector 42 and the magnetic selector 17, and position detection is made based on the magnetic field intensities detected by the reference device and the selected devices. The configuration, however, is not essential to the invention. For example, it is also possible to calculate the distance from the test capsule 2 or capsule endoscope 25 based on detected intensities with respect to all of the magnetic detectors 6a to 6h and generate eight ways of equations similar to Equations (2) to (5) to calculate the position of the test capsule 2 or the like. In the case of the configuration, computation using, for example, the least square method is possible. Thus, there is an advantage such that an error of derivation of the position of the test capsule 2 or the like can be further reduced.

Similarly, in the second embodiment, for example, the orientation direction of the capsule endoscope 25 may be derived via the plural magnetic detectors 6. That is, it is also preferable to derive the orientation direction at the plural magnetic detectors 6 by the above described method and to find the average of the derived orientation directions, to realize more accurate derivation of the orientation direction. Same applies to the detection of the position of the device, for which a plurality of position detections may be performed with the magnetic detector 6 or the like, and the average of the obtained positions may be found.

Although the function executing unit 32 having the CCD 30 and the like as an image capturing unit and the LED 28 and the like as an illuminating unit has been described in the second embodiment, the function executing unit 32 may obtain, in addition to the above, information of pH and the temperature in the subject 1. A configuration that the device to be introduced in a subject has an oscillator to capture an ultrasonic image of the inside of the subject 1 may be also employed. Further, a plurality of pieces of information may be obtained from the information of the inside of the subject.

The radio signal output from the power supply antennas $B_1$ to $B_m$ is not always limited to a signal obtained by multiplexing the control information signal and the power supply signal. Further, radio transmission from the position transducer to the capsule endoscope may not be performed. The power supply signal and a signal other than the control information signal may be multiplexed and the resultant signal may be transmitted. The position transducer 26 may receive only the radio signal output from the capsule endoscope. It is also possible to provide a storage unit in the capsule endoscope and, after the capsule endoscope is excreted to the outside of the subject, read information from the storage unit.

Further, in the second embodiment, the selection of the power supply antennas $B_1$ to $B_m$ has not been referred to particularly, however, as with the receiving antennas $A_1$ to $A_n$, the most suitable one may be selected based on the position and orientation direction of the capsule endoscope 25 to perform radio transmission. That is, in order to improve the supply efficiency of power supply signals or the like, not the transmission of radio signals uniformly from all of the power supply antennas, but selection of an antenna in response to the orientation direction or the like of the receiving antenna unit 36 provided within the capsule endoscope 25 can be performed using the orientation direction or the like of the capsule endoscope 25.

As is clear from the foregoing, the system according to the present invention is useful in connection with the swallowable capsule endoscope employed for the medical treatment, and particularly suitable for a device to be introduced into a subject, such as a patient, for the position detection.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A system comprising:
   a device that is adapted to be swallowed and passed though a subject to collect information on the subject, and includes a magnetic filed generator generating a magnetic field of a predetermined intensity; and
   a position transducer that include:
      a plurality of magnetic detectors, disposed substantially at the vertexes of a hypothetical cube circumscribing a part of the subject, for each detecting a magnetic field caused by the magnetic field generator;
      a storage unit that stores at least an intensity of a noise magnetic field component detected by each of the magnetic detectors with the magnetic detectors so oriented as to enable a parallel displacement thereof onto a predetermined coordinate system;
   a magnetic field extractor for coordinate-transforming the noise magnetic field components on the basis of a relationship between the predetermined coordinate system and a current coordinate system expended by selected ones of the magnetic detectors, and for extracting a magnetic field at each magnetic detector which magnetic field is caused by the magnetic field generator by removing a coordinate-transformed noise magnetic field component associated with detected magnetic fields detected by the selected magnetic detectors from the detected magnetic field detected by the magnetic detector; and
   a position processor for calculating a position of the device in the subject based on intensities of extracted magnetic fields extracted by the magnetic field extractor,
   wherein the system utilizes collected information obtained from the device by associating the collected information with the calculated position of the device.

2. The system according to claim 1, wherein the storage unit stores at least an earth magnetic component as the noise magnetic field component.

3. The system according to claim 1, wherein the position transducer further includes a vertical direction sensor that senses a relation between a vertical direction and one coordinate axis of the current coordinate system expanded by the selected magnetic detectors, and a horizontal in-plane azimuth sensor that senses a relation between an azimuth in a reference horizontal plane and the current coordinate system, and the magnetic field extractor calculates a differential value in each azimuth between the detected magnetic field detected by the magnetic detector for the azimuth and the corresponding noise magnetic field component stored for the azimuth in the storage unit based on a relation between sensed values from the vertical direction sensor and the horizontal in-plane azimuth sensor.

4. The system according to claim 3, wherein the magnetic detectors are disposed and fixed on the subject, and the vertical direction sensor includes an inclination sensor that senses an inclination of the subject with respect to a vertical direction.

5. The system according to claim 1, wherein the magnetic field generator is disposed in the device such that the magnetic field is output from the magnetic field generator in a vertical direction, and the magnetic field extractor extracts a magnetic field component in the vertical direction from the detected magnetic field detected by each magnetic detector.

6. The system according to claim 1, wherein the position processor includes a distance calculator calculating a distance between the device and each of the magnetic detectors based on an intensity of the detected magnetic field detected by the magnetic detector, and a position calculator for calculating the position of the device in the subject based on the calculated distances.

7. The system according to claim 1, wherein the magnetic field generator is disposed such that a direction of the magnetic field is fixed, and the position transducer further includes an orientation direction detector detecting an orientation direction of the device in the subject based on a travel direction of the extracted magnetic field extracted for a selected one of the detected magnetic fields by the magnetic field extractor.

8. The system according to claim 7, wherein the position transducer further includes an orientation direction database that stores, in advance, a relation between a distance from the magnetic field generator, a direction of the magnetic field, and an orientation direction of the device in the subject, and the orientation direction detector detects the orientation direction of the device in the subject based on the relation stored in the orientation direction database.

9. The system according to claim 1, wherein the device further includes a predetermined function executing unit that obtains information of the inside of the subject, and a radio transmitting unit that wirelessly transmits the information of the inside of the subject, and the position transducer further includes a receiving unit that receives a radio signal transmitted from the radio transmitting unit.

10. The system according to claim 9, wherein the position transducer includes the plurality of receiving units that receive a radio signal transmitted from the radio transmitting unit, and the position transducer further includes an orientation direction detector detecting an orientation direction of the device in the subject based on a travel direction of the corrected magnetic field corrected by the magnetic field extractor, and a selector selecting the receiving unit used for receiving the radio signal based on the position calculated by the position processor and the orientation direction detected by the orientation direction detector.

11. The system according to claim 10, wherein the function executing unit includes an illuminating unit that illuminates an inside of the subject, and an image capturing unit that captures an image of a region illuminated by the illuminating unit.

12. The system according to claim 9, wherein the function executing unit includes an illuminating unit that illuminates an inside of the subject, and an image capturing unit that captures an image of a region illuminated by the illuminating unit.

13. The system according to claim 12, wherein the position transducer further includes a storage unit that stores an image captured by the image capturing unit and the position of the device at a time when the image is captured, so that the image and the position are associated with each other.

14. The system according to claim 1, wherein the device is a capsule endoscope.

15. The system according to claim 1, wherein the storage unit stores information on the noise magnetic field component on the basis of a coordinate system.

* * * * *